US00PP21932P2

(12) United States Plant Patent
Korlipara

(10) Patent No.: US PP21,932 P2
(45) Date of Patent: May 24, 2011

(54) *ECHINACEA* PLANT NAMED 'FLAME THROWER'

(50) Latin Name: ***Echinacea* spp.**
Varietal Denomination: Flame Thrower

(75) Inventor: Harini Korlipara, Canby, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 21 days.

(21) Appl. No.: 12/653,641

(22) Filed: Dec. 14, 2009

(51) Int. Cl.
*A01H 5/00* (2006.01)

(52) U.S. Cl. ..... Plt./428

(58) Field of Classification Search ..... Plt./428
See application file for complete search history.

*Primary Examiner* — Wendy Haas
(74) *Attorney, Agent, or Firm* — Klarquist Sparkman, LLP

(57) ABSTRACT

A new and distinct *Echinacea* plant named 'Flame Thrower' characterized by medium large bicolor orange and red ray florets, dark cones, free flowering, well-branched flower stalks, early bloom time, and excellent vigor.

1 Drawing Sheet

Botanical denomination: *Echinacea* spp.

Variety designation: 'Flame Thrower'.

The present invention relates to a new and distinct cultivar of *Echinacea* and given the cultivar name 'Flame Thrower'. *Echinacea* is in the family *Asteraceae.* This new cultivar originated as a fourth generation seedling from a planned breeding program using the unpatented parents *Echinacea paradoxa* and *Echinacea purpurea* 'Ruby Giant' for the initial cross. The exact parents of this selection are unnamed proprietary, unreleased plants.

Compared to *Echinacea* 'Ruby Giant', an unpatented plant and the original seed parent in the breeding line, the new variety has red orange rather than red purple flowers.

Compared to *Echinacea paradoxa,* an unpatented plant and the original pollen parent in the breeding line, the new variety is red orange rather than yellow and has ray florets slightly rather than strongly reflexed.

This new *Echinacea* cultivar is distinguished by:

1. bicolor orange and red ray florets,
2. dark cones,
3. free flowering, well-branched flower stalks,
4. early bloom time,
5. excellent vigor.

This new cultivar has been reproduced only by asexual propagation (division and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the flowers of *Echinacea* 'Flame Thrower'.

FIG. 2 shows a 1 and a half year old plant growing in the ground in full sun in the field in summer in Canby, Oreg.

DETAILED PLANT DESCRIPTION

The following is a detailed description of the new *Echinacea* cultivar based on observations of 2 year old specimens growing in the ground in the field in full sun under typical outdoor conditions in Canby, Oreg. Canby is in Zone 8 on the USDA Hardiness map. Temperatures range from a high of 95 degrees F. in August to an average of 32 degrees F. in January. Normal rainfall in Canby is 42.8 inches per year in the trial fields in Canby, Oreg. The color descriptions are all based on The Royal Horticultural Society Colour Chart.

Plant:

*Type.*—Herbaceous perennial.
*Hardiness.*—USDA Zones 4 to 9.
*Size.*—90 cm wide and 72 cm tall to top of flowers.
*Form.*—Basal clump.
*Vigor.*—Excellent.
*Roots.*—Thickened, fibrous, with many downward growing and few laterals, ivory in color, Yellow White 158D, roots develop easily from cuttings from the crown.

Stem (flowering):

*Type.*—Ascending.
*Size.*—Branching to 83 cm tall to a terminal flower and 8 mm wide at base; each stem branching up to 6 times.
*Internode length.*—2 to 10 cm long.
*Surface texture.*—Strigose.
*Color.*—Yellow Green 146C mottled with Yellow Green 146B.

Leaf (basal):

*Type.*—Simple.
*Shape.*—Lanceolate.
*Arrangement.*—Basal.
*Blade size.*—Grows to 19.5 cm long and 6.4 cm wide.
*Margins.*—Shallowly broadly serrate.
*Apex.*—Acute.
*Base.*—Attenuate, continuing down petiole, clasping.
*Surface texture.*—Strigose on both sides.
*Venation.*—Pinnate.

*Color.*—Topside, Yellow Green 147A with the vein Yellow Green 145C; bottom side closest to Yellow Green 147B with the vein Yellow Green 145C.

*Petiole description.*—Grows to 15 cm long and 4 mm wide, strigose, Yellow Green 147D.

Leaf (stem):

*Type.*—Simple.

*Shape.*—Lanceolate.

*Arrangement.*—Alternate.

*Blade size.*—Grows to 15.2 cm long and 3.2 cm wide.

*Margins.*—Entire.

*Apex.*—Acute.

*Base.*—Attenuate, continuing down petiole, clasping.

*Surface texture.*—Strigose on both sides.

*Venation.*—Pinnate.

*Color.*—Topside, Yellow Green 147A with the vein Yellow Green 145C; bottom side closest to Yellow Green 147B with the vein Yellow Green 145C.

*Petiole description.*—Grows to 8.5 cm long and 5 mm wide, strigose, Yellow Green 147D, becoming shorter until no petioles on uppermost leaves.

Inflorescence:

*Type.*—Composite on terminal stalked heads.

*Number of flowering stems per plant in summer.*—9 to 18.

*Flowering stem.*—Grows to 83 cm tall from the base of the plant to the terminal flower and can grow to 22 cm long from the top leaf to the base of a flower head; branched, about 5 flowers per stem; diameter growing to 8 mm wide near the flower head; strigose, Yellow Green 146C mottled with Yellow Green 146B.

*Size.*—Grows to 9.5 cm wide and 6 cm deep as disc enlarges.

*Form.*—Ray petals cup downward slightly, mature disc is conic.

*Immature inflorescence.*—3 cm wide and 2 cm deep, ray florets held at a 100 degree angle and rolled up so only the back color shows, Greyed Orange 163C on outside and Greyed Orange 165C on the inside.

*Ray florets.*—Without pistil or stamen, 21 to 25 in number, oblanceolate with the tip two toothed (each acute), entire margins, base attenuate, grows to 4.5 cm long and 8 mm wide, glabrous on both sides; topside color of young mature ray florets changes from Orange 23A on top ⅓ to Orange 24A on middle ⅓ to Orange Red 34A on bottom ⅓, mature ray florets are Orange 23A on top ⅔ to Orange Red 34A on bottom ⅓.

*Disc.*—Slightly convex becoming conic, becoming 35 mm long and 44 mm wide with maturity, overall color Brown 200A in background with showy bracts Greyed Purple 185A.

*Disc florets.*—About 400 in number, each 7 mm long and 1.5 mm wide, each with one persistent, very stiff bract (8 mm long, Greyed Purple 187A on tip, Greyed Purple 185A on top half, Green 138A on bottom half); corolla 5 mm long and 1.2 mm wide, 5 lobed, glabrous, young corollas Greyed Yellow 162A on bottom half to Greyed Red 182A on top half, mature corollas Greyed Purple 185A; pistil 7 mm long, ovary 2.5 mm long, White 155A, style 4 mm long Black 202A, with an extruding, 2-branched stigma spreading 3.5 mm wide, Greyed Purple 187A; stamen 4 in number, 8 mm long, anthers 4 mm long and Black 202A, filaments 4 mm long, Yellow White 158D, pollen Yellow Orange 23A.

*Phyllaries.*—In 4 leafy series, area 3.7 cm wide and 15 mm deep, lobes lanceolate in shape, reflexed, grow to 18 mm long and 3 mm wide, Yellow Green 147B, margins strigose, tip acute.

*Receptacle.*—Grows to 12 mm wide and 18 mm deep, White 155A.

*Bloom period.*—July through October in Canby, Oreg.

*Fragrance.*—Lovely, floral.

*Lastingness.*—Each inflorescence lasts about two weeks in Canby, Oreg.

Seeds: average number of 6 seeds/head, each 5 mm long and 2.5 mm wide, oval, Brown 200C

*Fertility.*—Good.

Disease and pests: *Echinacea* are susceptible to leaf miners, powdery mildew, bacterial spots, and gray mold. None of these have been observed on plants grown under commercial conditions in Canby, Oreg. No resistance is known.

I claim:

1. A new and distinct *Echinacea* plant as herein illustrated and described.

* * * * *

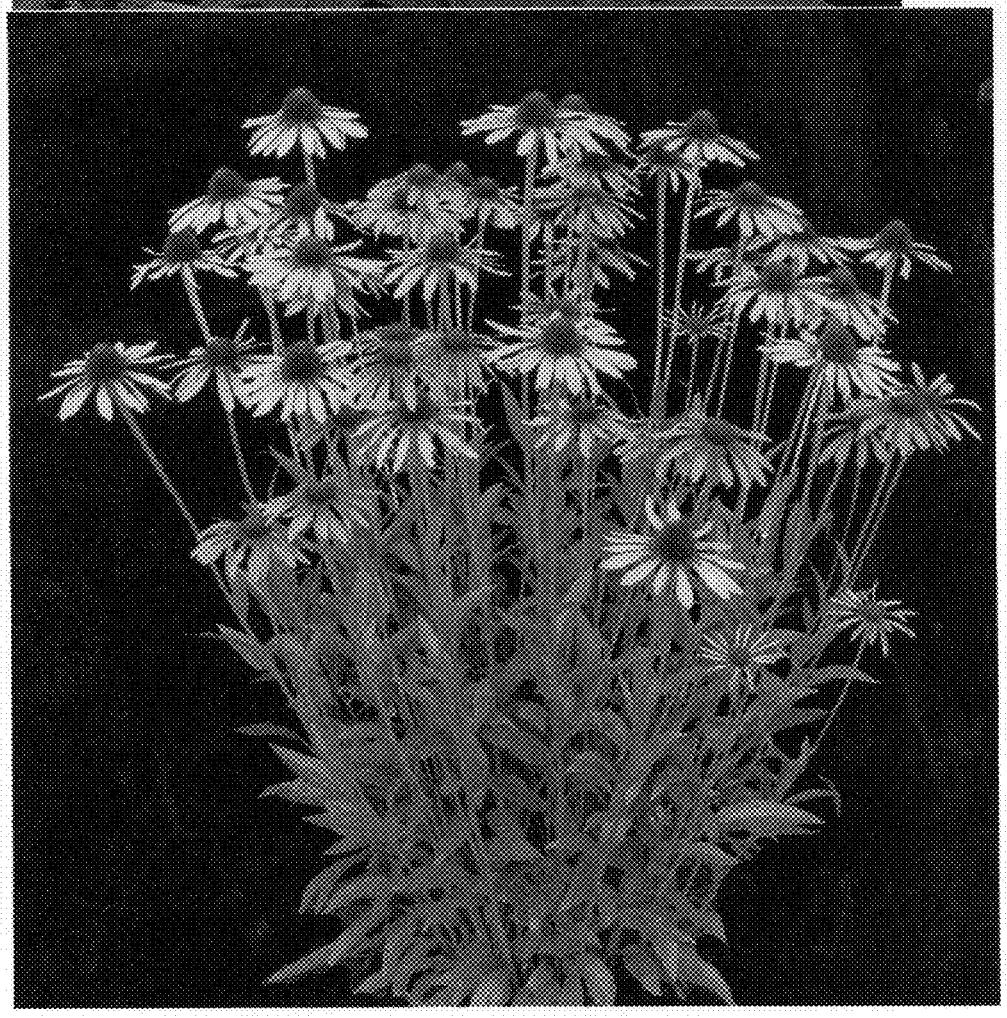

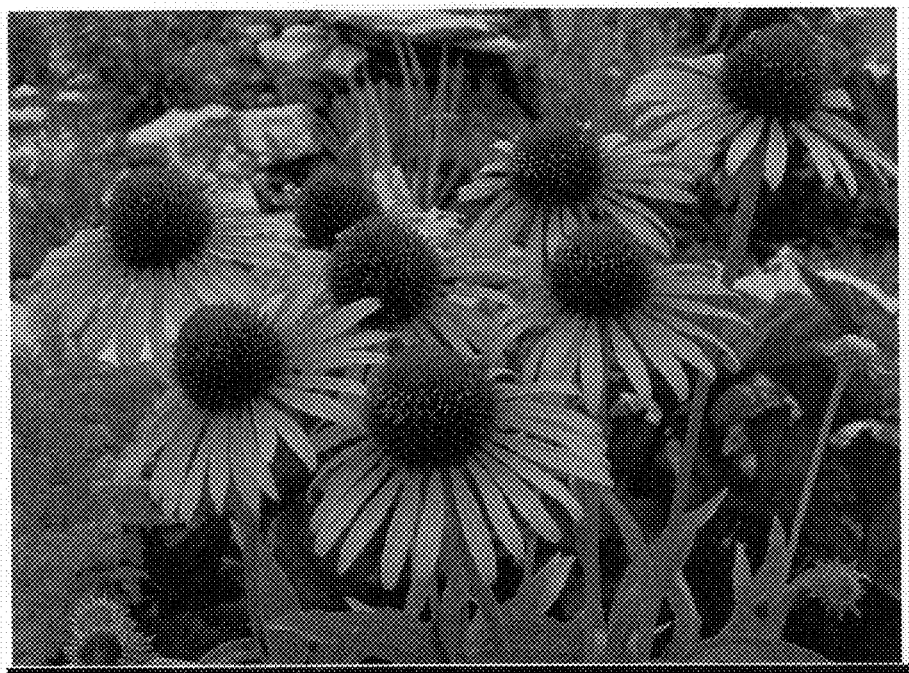
Figure 1 above
Figure 2 below